(12) United States Patent  
DeCarlo (10) Patent No.: US 8,037,895 B2
(45) Date of Patent: Oct. 18, 2011

(54) COOLANT LINE CLIP ASSEMBLIES FOR USE WITH FLUID DELIVERY SYSTEMS

(75) Inventor: Arnold V. DeCarlo, Frederick, CO (US)

(73) Assignee: Vivant Medical, Inc., Boulder, CO (US)

( * ) Notice: Subject to any disclaimer, the term of this patent is extended or adjusted under 35 U.S.C. 154(b) by 736 days.

(21) Appl. No.: 12/123,645

(22) Filed: May 20, 2008

(65) Prior Publication Data

US 2009/0289151 A1    Nov. 26, 2009

(51) Int. Cl.
*F16L 3/02* (2006.01)
(52) U.S. Cl. .......... 137/15.01; 137/316; 24/522; 248/49
(58) Field of Classification Search ............... 137/15.01, 137/315.01, 316; 604/533, 905; 24/522, 24/910; 248/49
See application file for complete search history.

(56) References Cited

U.S. PATENT DOCUMENTS

| | | |
|---|---|---|
| 1,911,229 A | 2/1932 | Gleim |
| 3,942,528 A | 3/1976 | Loeser |
| 4,435,174 A | 3/1984 | Redmond et al. |
| D273,993 S | 5/1984 | Schulte et al. |
| 4,645,492 A | 2/1987 | Weeks |
| 4,758,174 A | 7/1988 | Michaels et al. |
| 4,802,864 A | 2/1989 | Michaels et al. |
| 5,192,273 A | 3/1993 | Bierman et al. |
| 5,314,411 A | 5/1994 | Bierman et al. |
| D350,201 S | 8/1994 | Hirsch et al. |
| 5,354,282 A | 10/1994 | Bierman |
| 5,456,671 A | 10/1995 | Bierman |
| 5,578,013 A | 11/1996 | Bierman |
| 5,620,333 A | 4/1997 | Boyle |
| 5,640,476 A | 6/1997 | Womack et al. |
| 5,672,847 A | 9/1997 | Piatt |
| 5,690,616 A | 11/1997 | Mogg |
| 5,702,371 A | 12/1997 | Bierman |
| 5,710,851 A | 1/1998 | Walter et al. |
| 5,860,952 A | 1/1999 | Quinn |
| 5,890,926 A | 4/1999 | Pauza et al. |
| 5,910,128 A | 6/1999 | Quinn |
| 5,916,199 A | 6/1999 | Miles |
| 5,947,931 A | 9/1999 | Bierman |
| 5,957,894 A * | 9/1999 | Kerwin et al. ............... 604/178 |
| 6,001,081 A | 12/1999 | Collen |
| 6,013,875 A | 1/2000 | Fridenberg et al. |
| 6,036,673 A | 3/2000 | Quinn |
| 6,159,198 A | 12/2000 | Gardeski et al. |
| 6,427,953 B1 | 8/2002 | Dickens |
| 6,428,515 B1 | 8/2002 | Bierman et al. |
| 6,477,770 B1 | 11/2002 | Dickens |
| 6,544,247 B1 | 4/2003 | Gardeski et al. |
| 6,554,489 B2 | 4/2003 | Kent et al. |
| 6,634,801 B1 | 10/2003 | Waldron et al. |
| 6,695,490 B2 | 2/2004 | Shirakawa et al. |

(Continued)

*Primary Examiner* — Kevin Lee (57) ABSTRACT

The present disclosure provides a fluid clip for use with a coolant system for electrosurgical procedures. The fluid clip includes a clip housing having proximal and distal ends and a channel defined therethrough. The channel is dimensioned to receive tubing for carrying a cooling fluid from a cooling source. The fluid clip includes a luer that includes a passageway defined therethrough. The passageway is dimensioned to securely receive the tubing such that the tubing extends through the luer for reception within the channel defined in the clip housing. The luer includes one or more interface on a surface thereof that matingly engages a corresponding interface on the clip housing. The interface on the luer cooperates with the interface on the clip housing to limit rotation of the tubing.

20 Claims, 8 Drawing Sheets

U.S. PATENT DOCUMENTS

| | | |
|---|---|---|
| 6,808,315 B2 | 10/2004 | Asada |
| 6,817,780 B2 | 11/2004 | Ngo |
| 6,878,136 B2 | 4/2005 | Fleury et al. |
| 6,918,894 B2 | 7/2005 | Fleury et al. |
| 6,932,515 B2 | 8/2005 | Ngo |
| D525,359 S | 7/2006 | Stephens |
| 7,198,066 B2 | 4/2007 | Kagenow |
| D543,277 S | 5/2007 | White |
| 7,229,051 B2 | 6/2007 | Mailhot, Jr. |
| 7,312,407 B2 | 12/2007 | Case |
| 7,354,421 B2 | 4/2008 | Bierman |
| 7,799,015 B2 * | 9/2010 | Schweikert .................. 604/533 |

* cited by examiner

COOLANT LINE CLIP ASSEMBLIES FOR USE WITH FLUID DELIVERY SYSTEMS

BACKGROUND

1. Technical Field

The present disclosure relates to fluid delivery systems. More particularly, the present disclosure relates to coolant line clip assemblies for use with coolant delivery systems configured for delivering and circulating a quantity of coolant.

2. Description of Related Art

Microwave antennas are used for various types of tissue ablation procedures. Typically, microwave antennas include a probe configured to deliver thermal microwave energy to tissue for ablation purposes. Microwave antennas may include and/or be in operative communication with a coolant delivery system configured to circulate coolant (e.g., sterile water) from the microwave generator and/or coolant delivery system to the probe via a flexible coolant line. Chilling the probe allows the antenna and transmission lines associated with the probe to operate at higher powers over an extended period of time. Chilling of the antenna portion also allows for a greater depth of penetration of the probe. Moreover, by cooling an outer probe surface around the antenna, the therapeutic heating radius is increased.

It is also known that lesions created by microwave antennas typically yield tear drop profiles resulting in so called "tracking" caused by conductive energy which tracks proximally beyond the antenna. Cooling the antenna may help eliminate this profile and may provide for a more elliptical to spherical lesion with limited tracking. All of these design features translate into large, controllable lesions.

Commercially available coolant lines configured for use with coolant delivery systems are typically made from lightweight flexible material (PVC for example) that is formed into suitable lengths of tubing. Unfortunately, because the tubing is made from lightweight material that is made to easily flex, inadvertent blockages may develop along the length of the tubing. For instance, practitioners pulling on the coolant line may cause kinks to form along the length of the tubing and, or in addition thereto, the weight of the tubing may cause the tubing to collapse. Either instance may result in impeding and/or preventing circulation of the coolant to a probe during a microwave ablation procedure, which, in turn, may result in the microwave generator shutting off prematurely and/or result in the probe becoming too hot and overheated, which, in turn, may result in the unnecessary burning of tissue.

SUMMARY OF THE DISCLOSURE

A coolant line clip capable of preventing blockages from developing along the length of the coolant line, while allowing maximum coolant flow through the probe to facilitate tissue ablation would be useful in microwave ablation and/or other surgical procedures requiring coolant lines.

Therefore, the present disclosure provides a fluid clip for use with a coolant system for electrosurgical procedures. The fluid clip includes a clip housing that is substantially J-shaped defining a radius at the distal end thereof and is dimensioned to prevent the tubing from kinking. The fluid clip housing has proximal and distal ends and a channel defined therethrough. The distal end of the clip housing includes a mechanical interface disposed thereon that facilitates secure engagement of the tubing therein. The channel is dimensioned to receive tubing for carrying a cooling fluid from a cooling source. The fluid clip includes a luer that includes a passageway defined therethrough. The passageway is dimensioned to securely receive the tubing such that the tubing extends through the luer for reception within the channel defined in the clip housing. The luer includes one or more interface on a surface thereof that matingly engages a corresponding interface on the clip housing. The interface on the luer cooperates with the interface on the clip housing to limit rotation of the tubing. In embodiments, the interface on the luer includes a pair of opposing wings that matingly engage a corresponding pair of slots defined within the clip housing.

In embodiments, the luer includes a housing having a proximal flange that extends therefrom and is moveable relative to the luer housing to secure the tubing within the passageway. In embodiments, the luer housing includes an inner peripheral surface that is dimensioned to crimp the proximal flange upon reception therein, which, in turn, secures tubing within the passageway.

In embodiments, the luer includes a housing having a proximal flange that extends therefrom. The proximal flange includes an inner peripheral surface that forms part of the passageway. Here, the inner peripheral surface is dimensioned to securely engage the tubing when the tubing is received therethrough.

In embodiments, the interface at the distal end of the hosing includes a pair of opposing flanges that cooperate to facilitate secure engagement of the tubing to the distal end of the clip housing.

In embodiments the interface at the distal end of the hosing includes a pair of opposing flanges that cooperate in an overlapping manner to facilitate secure engagement of the tubing to the distal end of the clip housing.

The present disclosure also provides a method of preventing kinking in tubing in an electrosurgical cooling system. The method includes the steps of providing a clip housing having proximal and distal ends and a channel defined therethough and a luer including a passageway defined therethrough. The channel and the passageway are dimensioned to receive tubing for carrying a cooling fluid from a cooling source. The method includes the steps of: inserting the tubing into and through the passageway in the luer and securing the luer to the tubing; inserting the tubing into and through the channel of the clip housing such that the tubing extends therefrom for engagement with a surgical instrument; and operatively engaging mating mechanical interfaces on the luer with corresponding mechanical interfaces on the clip housing to limit rotation of the tubing.

In an embodiment, the step of inserting the tubing into and through the passageway in the luer includes the step of crimping a portion of the luer to secure the tubing.

In an embodiment, the luer of the providing step includes a luer housing having a proximal flange that extends therefrom and the step of crimping includes the step of moving one of the luer housing and the proximal flange relative to one another to crimp the tubing.

In an embodiment, the method of preventing kinking in tubing in an electrosurgical cooling system further comprises the step of operatively engaging the tubing in the distal end of the clip housing.

The present disclosure further provides a coolant delivery system for use with a microwave antenna. The coolant delivery system includes one or more lengths of tubing having one end adapted to connect to a microwave antenna and a second end adapted to connect to a coolant reservoir configured to store at least one type of coolant. The coolant delivery system includes a clip housing having proximal and distal ends and a channel defined therethrough. The channel configured to receive the one or more lengths tubing for carrying a cooling fluid from the coolant reservoir. The coolant delivery system also includes a luer that includes a passageway defined therethrough. The passageway is configured to securely receive the one or more lengths of tubing such that the tubing extends through the luer for reception within the channel defined in the clip housing. The luer includes one or more interfaces on a surface thereof that matingly engage a corresponding interface on the clip housing to limit rotation of the tubing.

DETAILED DESCRIPTION

Detailed embodiments of the present disclosure are disclosed herein; however, the disclosed embodiments are merely examples of the disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure. In the drawings and in the descriptions that follow, the term "proximal," as is traditional, will refer to the end that is closer to the user, while the term "distal" will refer to the end that is farther from the user.

While the following describes a clip configured for use with fluid delivery systems that are operatively associated with microwave ablation systems, it will be appreciated by those skilled in the art, that the clip can be used with any fluid delivery system.

Figure 1:
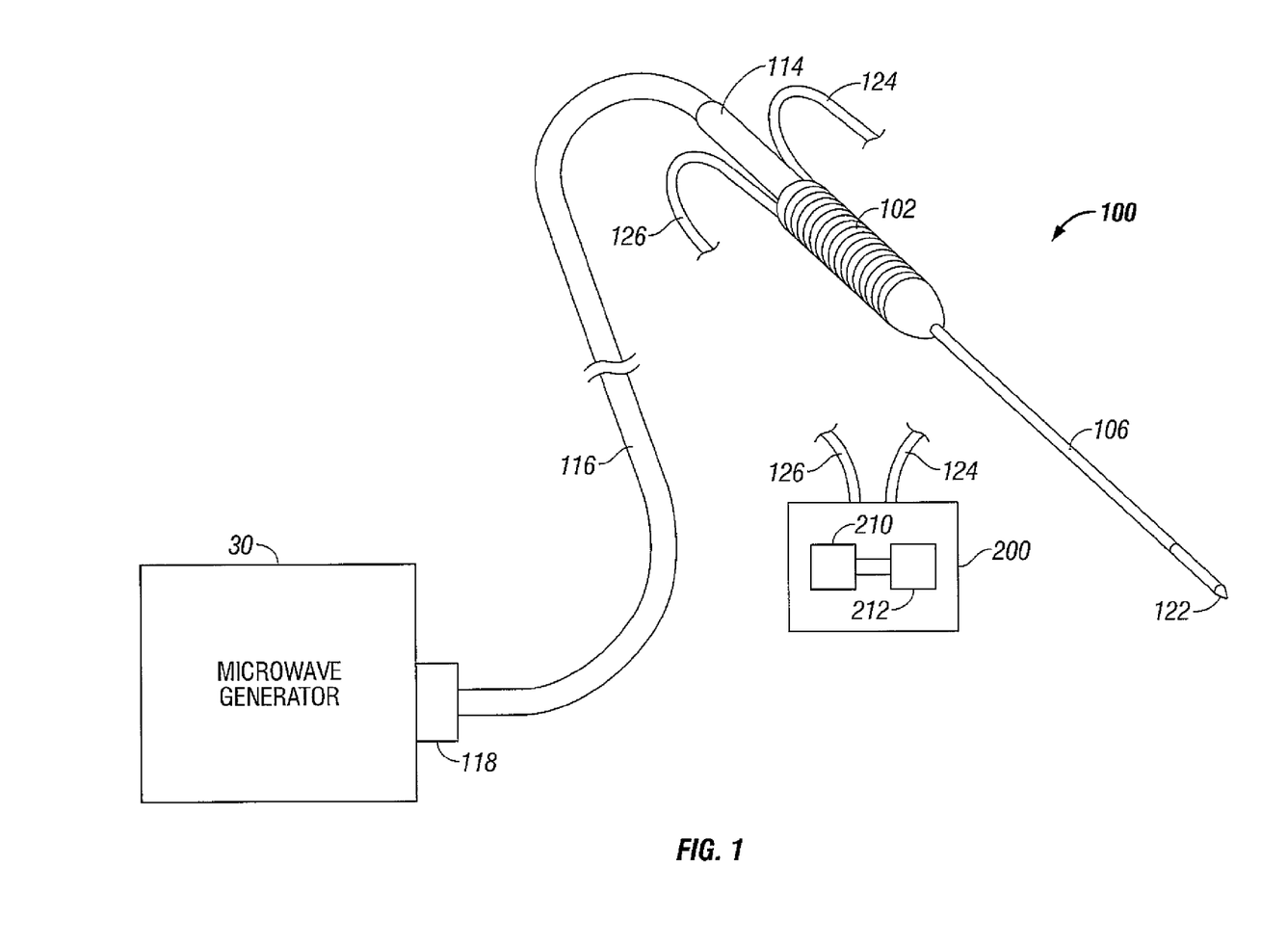
FIG. 1 is a perspective view of a microwave antenna assembly that employs a coolant delivery system in accordance with an embodiment of the present disclosure.
Figure 2:
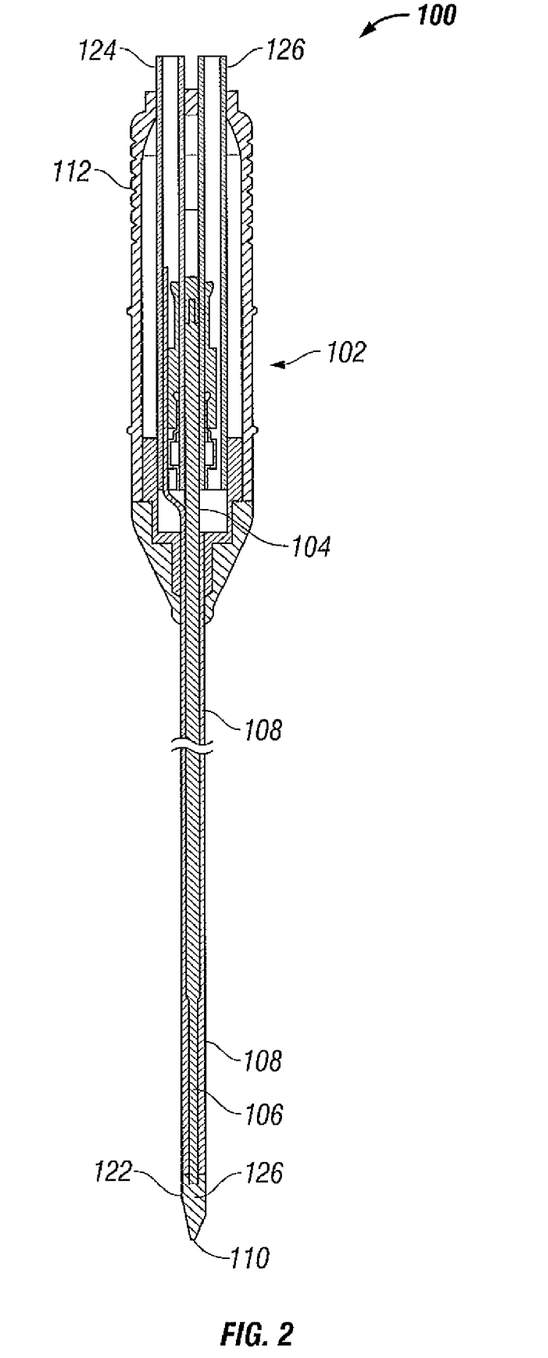
FIG. 2 is a cross-sectional view of the antenna assembly depicted in FIG. 1.

With reference to FIGS. 1 and 2, and initially with reference to FIG. 1, a representative diagram of a microwave antenna probe assembly 100 in operative communication with a coolant system 200 is shown. The probe assembly 100 includes a radiating portion 106 connected by a feedline 114 (or shaft) via a cable 116 that ultimately couples to a generator 30 via connector 118. Probe assembly 100, as shown, is a dipole microwave antenna assembly, but other suitable antenna assemblies, e.g., monopole or leaky wave antenna assemblies, may also be utilized. Radiating portion 106 includes a distal end 122 having a tapered end 126 (FIG. 2) that terminates at a tip 110 to facilitate insertion into tissue with minimal resistance. In those cases where the radiating portion 106 is inserted into a pre-existing opening, tip 110 may be rounded or flat.

Feedline 114 includes a coaxial cable made of a conductive metal which may be semi-rigid or flexible. Feedline 114 may also have a variable length from a proximal end of radiating portion 106 to a distal end of cable 116, depending on particular purpose.

With reference to FIG. 2, a cross-sectional side view of probe assembly 100 is shown. Although this variation illustrates the cooling of a straight probe antenna, a curved or looped microwave antenna may also utilize much of the same or similar principles. Probe assembly 100 includes a cooling handle assembly 102 having an elongate outer jacket 108 extending therefrom. Outer jacket 108 extends and terminates at tip 110. Microwave antenna 104 is positioned within handle assembly 102 such that the radiating portion 106 of antenna 104 extends distally into outer jacket 108 towards tip 110. As shown, inflow tubing 124 extends into a proximal end of handle body 112 and distally into a portion of outer jacket 108. Similarly, outflow tubing 126 extends from within handle body 112 such that the distal ends of inflow tubing 124 and outflow tubing 126 are in fluid communication with one another. In-flow tubing 124 and out-flow tubing 126 may be housed together within a casing or jacket (not explicitly shown).

The distal ends of inflow tubing 124 and outflow tubing 126 are positioned within handle body 112 such that coolant (e.g., sterilized water) may be pumped into handle body 112 via a pump 210 (FIG. 1) through inflow tubing 124. Coolant entering handle body 112 comes into direct contact with at least a portion of the shaft of antenna 104 to allow for convective cooling of the antenna shaft to occur. The coolant exits handle body 112 via outflow tubing 126 (FIG. 2).

With reference again to FIG. 1, the coolant is pumped, by way of pump 210, using any combination of positive and/or negative pressure through inlet tube 124 and outlet tube 126, respectively. In pumping the coolant through probe assembly 100, the coolant typically passes through probe assembly 100 at a uniform flow rate. In another variation, the flow rate may be intermittent such that a volume of coolant may be pumped and allowed to warm up by absorbing heat from the antenna. Temperature sensors (not explicitly shown), such as thermistors, thermocouples, etc may be incorporated within or openly associated with the outer jacket 108 to sense the fluid and/or outer jacket 108 temperatures. The coolant delivery system may be configured to automatically pump additional coolant into antenna assembly 100 once the sensed temperature reaches a predetermined level or it may be configured to notify the user via an audible or visual alarm.

The coolant is stored in reservoir 212 and has a temperature that varies depending upon desired cooling rates and the desired tissue impedance matching properties. Biocompatible coolants having sufficient specific heat values for absorbing heat generated by microwave ablation antennas may be utilized, e.g., liquids including, but not limited to, sterile water, saline, Fluorinert, liquid chlorodifluoromethane, and so on. In another variation, gases (such as nitrous oxide, nitrogen, carbon dioxide, etc.) may also be utilized as the coolant.

For a more detailed description of probe assembly 100 and coolant delivery system 200, and operative components associated therewith, reference is made to commonly owned U.S. patent application Ser. No. 11/053,987, filed on Feb. 8, 2005, entitled "DEVICES AND METHODS FOR COOLING MICROWAVE ANTENNAS."

As noted above, clip 300 is adapted to couple to one or more coolant lines (e.g., inflow tube 124 and/or outflow tube 126) of coolant delivery system 200 for use with microwave probe antenna assembly 100. To facilitate understanding of the structural and operative features of clip 300, clip 300 is described in terms of use with in-flow tube 124.

Figure 3A:
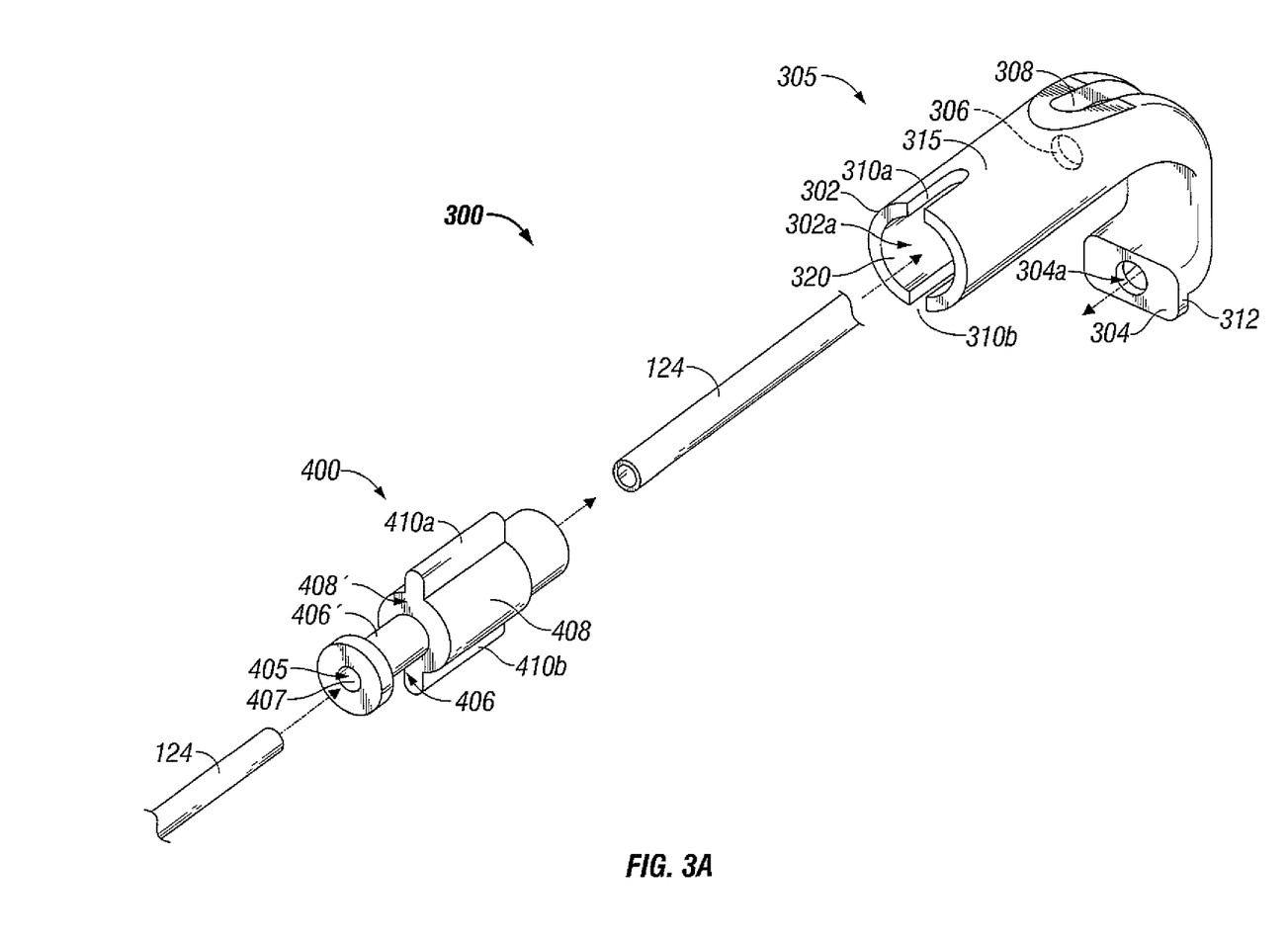
FIG. 3A is an exploded, perspective view of a coolant line clip and a length of tubing including a luer fitting for use with the coolant delivery system depicted in FIG. 1 in accordance with an embodiment of the present disclosure.
Figure 3B:
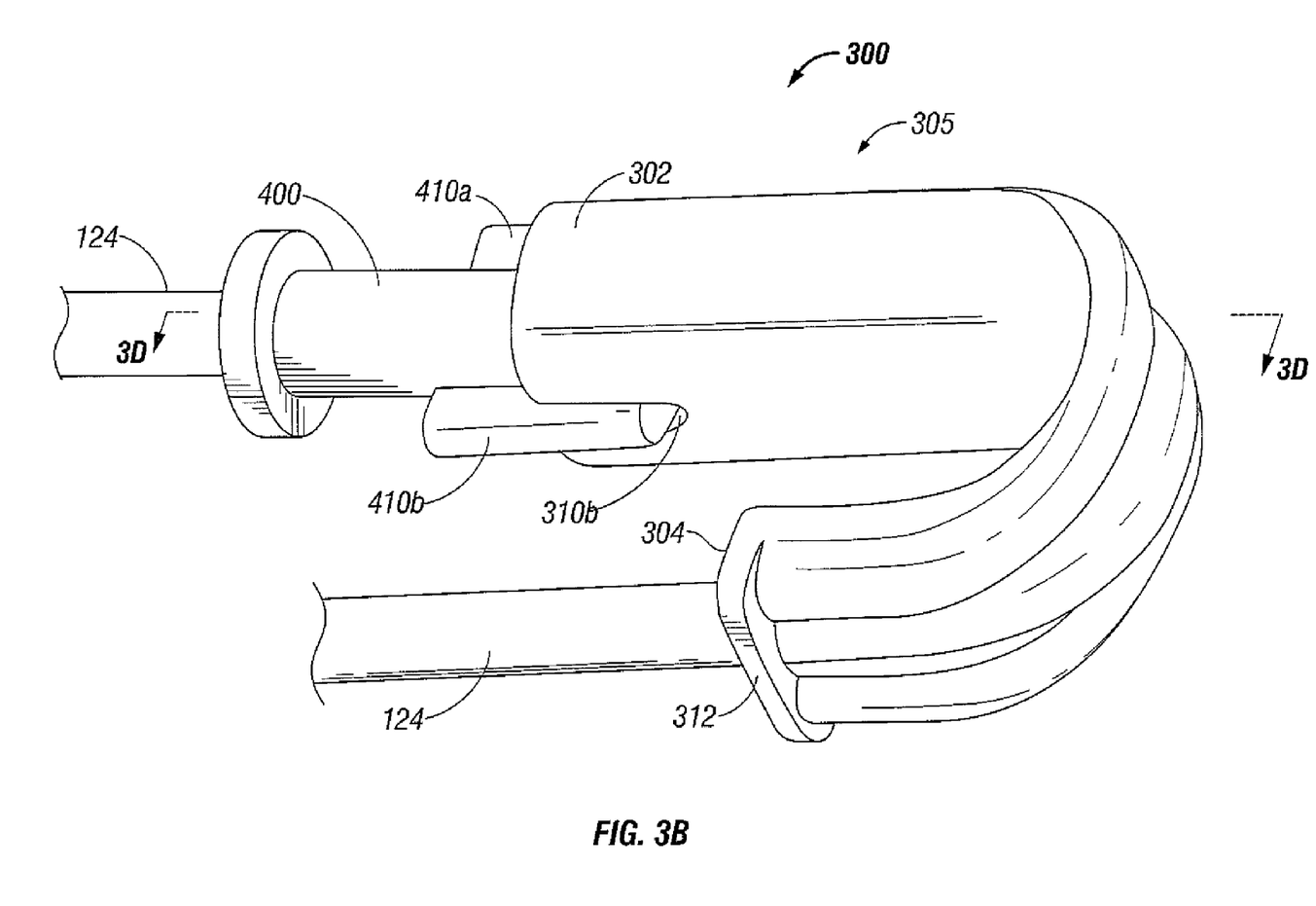
FIG. 3B is a front, perspective view of the coolant line clip connected to the length of tubing depicted in FIG. 3A.

With reference to FIGS. 3A-3E, and initially with reference to FIG. 3A, clip 300 is shown and configured to support tubing 124 of coolant system 200. Clip 300 includes a clip housing 305 having first and second ends, 302 and 304, located respectively, at proximal and distal ends thereof. Ends 302 and 304 are configured such that tubing 124 remains in a substantially fixed position along a curve or contour of clip housing 305 during normal operation thereof. Each of the ends 302, 304 includes respective first openings 302a and 304a. Clip housing 305 also includes a radius "R" (FIG. 3D) that allows tubing 124 to flex while coolant flows therethrough. A channel 308 is defined in clip 300 and extends from first and second openings, 302a and 304a, respectively, to provide support for tubing 124. Clip housing 305 also includes one or more mechanical interfaces 312 disposed at proximate first and second ends 302 and 304.

Figure 3C:
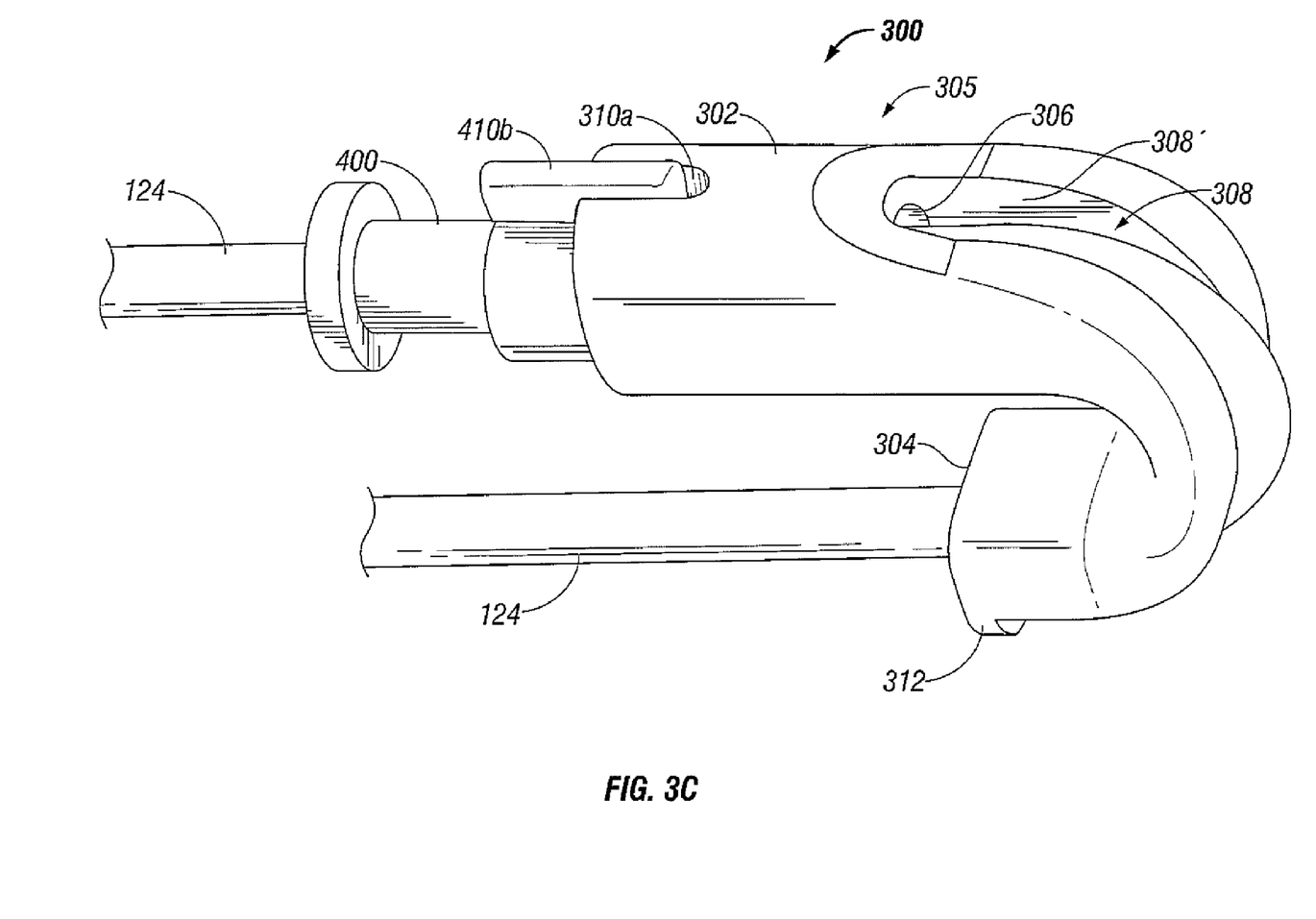
FIG. 3C is a side, perspective view of the coolant line clip connected to the length of tubing depicted in FIG. 3B.
Figure 3D:
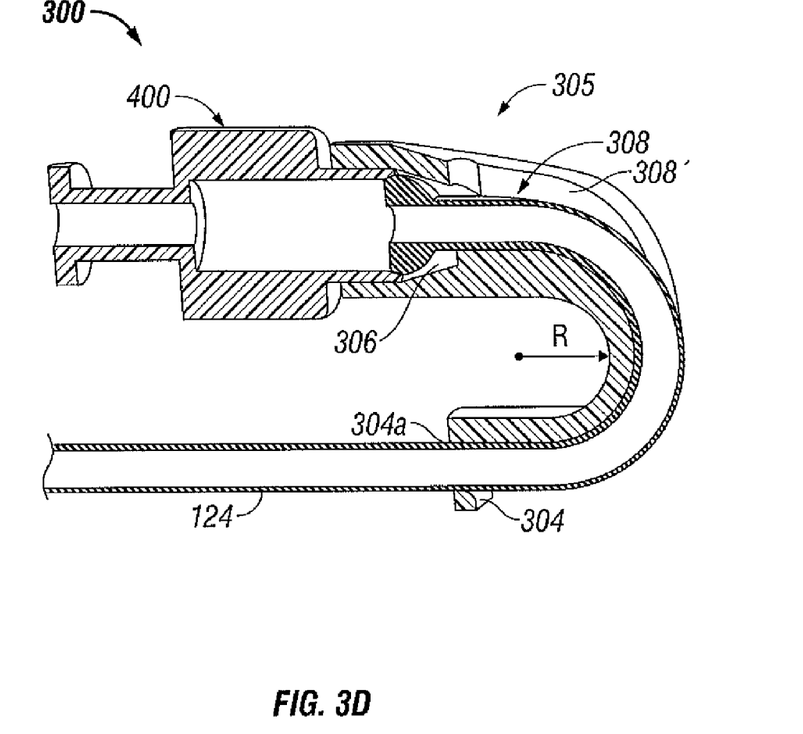
FIG. 3D is a cross-sectional view of the coolant line clip depicted in FIG. 3B.
Figure 3E:
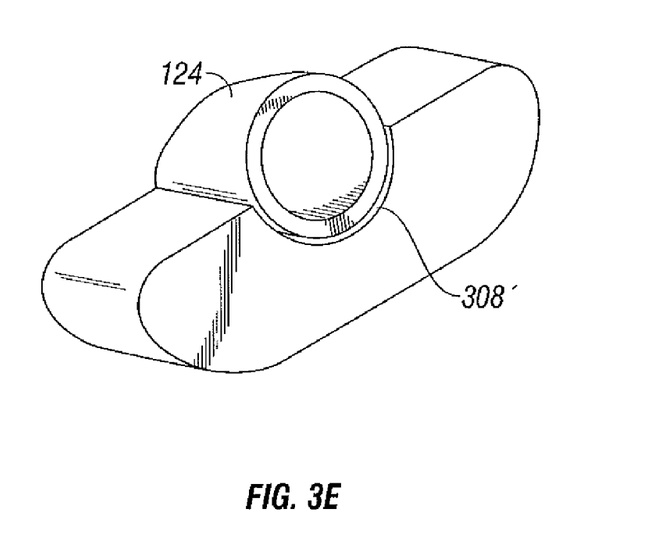
FIG. 3E is a partial cut-away view of the coolant line clip taken along the line segment "3E-3E" in FIG. 3B.

With continued reference to FIG. 3A, first opening 302a includes an outer periphery 315 defined to mechanically engage a luer fitting 400 (as explained below) and an inner periphery 320 having a suitable diameter for receiving tubing 124. First opening 302a also includes a substantially circumferential shape and extends within clip housing 305 toward a distal end thereof. The inner periphery may taper from the first proximal end 302 of clip housing 305 toward the second or distal end 304 to ensure a tight fit between tubing 124 and/or luer fitting 400 and opening 302a, as best seen in FIG. 3D. As described in detail below, a user connects tubing 124 to clip housing 305 by way of a press fit, interference or friction fit engagement. First opening 302a may include additional structure that facilitates attachment of the tubing 124 to clip housing 305, e.g., indents, detents, and the like (not explicitly shown). An opening 306 having a suitable diameter and configured to receive tubing 124 is defined at a distal end of inner periphery 320 of first opening 302a, as shown in FIG. 3C and FIG. 3A (in phantom).

As mentioned above, the outer periphery 315 includes a mechanical interface configured to engage a corresponding interface disposed on luer fitting 400. The interface may be any suitable structure, such as, for example, intents, detents, slits, slots and the like. As shown in FIG. 3A, the interface includes two opposing slots 310a and 310b each configured to engage corresponding wings 410a and 410b of the luer type fitting 400. When the luer fitting 400 is engaged on tubing 124 and coupled to slots 310a and 310b (see FIG. 3B), wings 410a and 410b prevent tubing 124 from twisting while tubing 124 is engaged with clip 300, reducing the risk of impeding coolant flow to and through the probe assembly 100. Other types of mechanical interface may be employed to accomplish similar purposes.

As shown in FIGS. 3A-3D, tubing 124 is initially inserted into a passageway 405 defined in luer fitting 400 such that the tubing extends therethrough for engagement with clip housing 305 as explained in more detail below. Proximal flange 406 is configured for slideable reception within luer housing 408 and includes an outer surface 406' having a generally circular shape that is dimensioned to slidingly engage an inner peripheral surface 408' of housing 408. Surface 408' may be tapered along a length thereof to facilitate engaging the tube within luer housing 408. Flange 406 also includes an inner periphery 407 that defines passageway 405. The tube 124 is secured by sliding flange 406 into luer housing 408 such that the tapered inner surface 408' of luer housing 406 crimps and secures the tube 124 in a uniformly concentric manner.

In one embodiment, inner periphery 407 may be tapered along a length thereof to facilitate securing the tube 124 within luer fitting 400. Alternatively, the outer surface 406' of flange 406 may be tapered such that the tube 124 is crimped and secured upon reception of the flange into luer housing 408. In this instance, inner peripheral surface 408' is not necessarily tapered.

In another embodiment, luer fitting 400 includes a housing 408 that includes an integrally-formed proximal flange 406 that extends therefrom. The proximal flange 406 receives the tube 124 for passage through passageway 405 for engagement with clip housing 305. In this instance, the tube 124 is permitted to rotate within the luer fitting 400 that may be suitable for a particular surgical purpose. However, the surgical instrument (not shown) may need a particularly-designed coupling (not shown) to avoid twisting the tube 124 during use.

As shown in FIGS. 3B-3E, once the tube is secured within the luer fitting 400, the distal end of the tube 124 is fed through opening 302a in clip housing 305, around channel 308, and through exit opening 304a disposed in end 304. The luer fitting 400 is then oriented such that the two opposing wings 410a and 410b align with the corresponding slots 310a and 310b, respectively, in clip housing 305 and moved into secure engagement therewith. In the particular embodiment described above wherein the tube is crimped within luer fitting 400, the engagement of the wings 410a and 410b within respective slots 310a and 310b prevents the tube 124 from twisting during use. Because the clip 300 and luer 400 assembly maintains the tubing 124 substantially fixed, movement of the probe 100 and/or the tubing 124 adjacent thereto will not cause the tubing to kink during normal operation thereof.

As shown in FIGS. 3A and 3C, channel 308 is configured to extend from opening 306 along a length of clip housing 305 to second opening 304a disposed in distal end 304. In the illustrated embodiment, the surface 308' of channel 308 is configured to provide support for tubing 124 within clip 300. The surface 308' of channel 308 has a diameter that is slightly greater than the diameter of tubing 124 such that tubing 124 easily rests therein. Alternatively, surface 308' may include a diameter that is slightly less than or equal to tubing 124 such that tubing 124 is further secured within clip housing 305. Channel 308 may be coated with a material that reduces static and kinetic coefficients of friction between the tubing 124 and the channel surface 308'. For example, channel surface 308' may be coated with nylon, TEFLON™ and the like. In an embodiment, channel 308 is open along a length of clip housing 305 to enable a visual confirmation of coolant flow, or lack thereof, through the tubing 124.

Channel 305 includes a generally J-shape having a suitable radius "R" that allows tube 124 to flex during operation of coolant delivery system 200 (see FIG. 3D). Radius "R" includes a sufficient diameter that provides adequate structural support for tubing 124, while providing clip housing 305 and, thus, tubing 124 some degree of flexibility.

Figure 4:
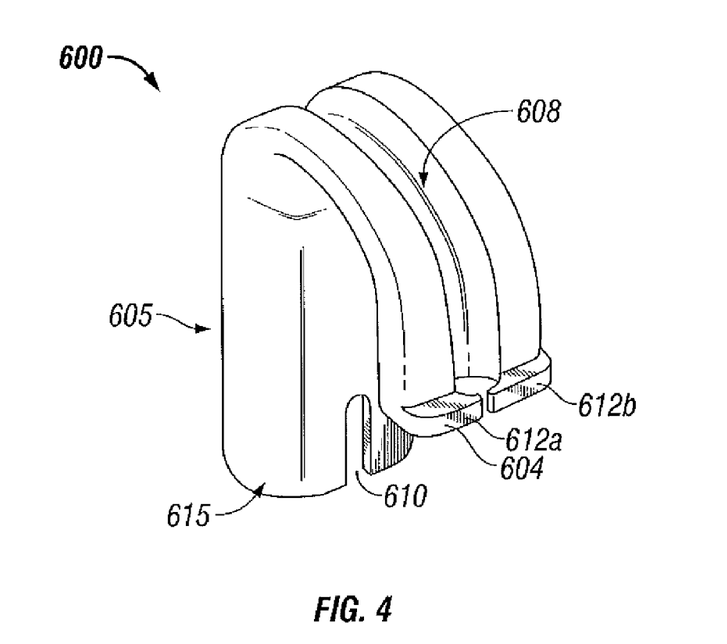
FIG. 4 is a perspective view of the coolant line clip that includes a line lock in accordance with another embodiment of the present disclosure.

As mentioned above and as shown in FIGS. 3A-3D, the distal end 304 includes an opening 304a extending therethrough that is dimensioned to mechanically engage the tubing 124 as the tubing extends therethrough. As shown in FIG. 4, an alternative clip 600 may be utilized. Clip 600 includes a clip housing 605, one or more slots 610, and a generally J-shaped support channel 608 (similar to the J-channel described above) that extends to a distal end 604. The distal end 604 includes a pair of opposing flanges 612a and 612b that are flexible to facilitate insertion of the tube 124 therein. The two opposing flanges 612a and 612b are preferably made from a semi-resilient material to flex inwardly or outwardly to facilitate insertion of the tube in the clip housing 605. The flanges 612a and 612b, in one instance, may be dimensioned to flex inwardly such that the tube 124 may be essentially snap-fit into secure engagement with the distal end 604. In another instance the flanges 612a and 612b may be dimensioned to flew outwardly (either together or independently) to facilitate secure engagement with the tube 124.

Figure 5:
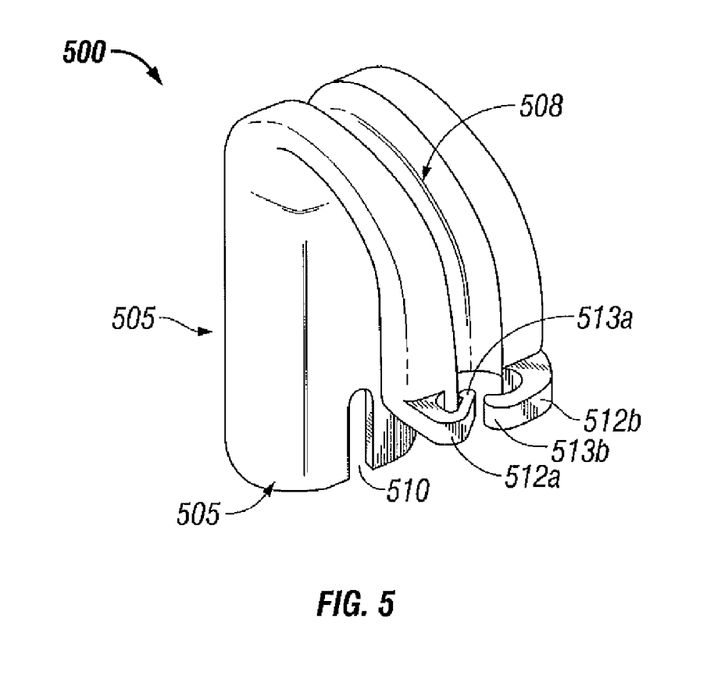
FIG. 5 is a perspective view of the coolant line clip that includes a line lock in accordance with an embodiment of the present disclosure.

FIG. 5 shows another embodiment of a clip 500 that includes a housing 505, one or more slots 510, and a generally J-shaped support channel 508 that extends to a distal end 504. The distal end 404 includes a pair of opposing flanges 512a and 512b that are flexible to facilitate insertion of the tube 124 therein. The two opposing flanges 512a and 512b are preferably made from a semi-resilient material to flex inwardly or outwardly to facilitate insertion of the tube in the clip housing 505. Flanges 512a and 512b are dimensioned to flex outwardly to secure tube 124 into secure engagement with the distal end 504. Flange 512a includes a distal end 513a that includes a mechanical interface, e.g., nub, is biased inwardly to enhance retention of the tube 124 within distal end 504. More particularly, upon insertion, tube 124 forces flange 512a outwardly past a distal end 513b of flange 512b and, once the tube 124 is seated within channel 508, the biasing overlapping force of flange 512a against flange 512b enhances the retention of both flanges 512a and 512b (with the distal ends 513a and 513b working in cooperation) against the tube 124.

Clip housing 305 and luer housing 405 may be made from any suitable material including but not limited to, metal, metal alloy, plastic, plastic composite, and the like. In embodiments, it may prove useful to fabricate clip housing 305 and luer housing 405 from one or more biocompatible materials such as, for example, silicone elastomer, polyvinyl chloride, natural or synthetic rubber, polyurethane and so on. Clip housing 305 and luer housing 405 may be formed by stamping, overmolding, injection molding, or by other suitable means known in the art.

From the foregoing and with reference to the various figure drawings, those skilled in the art will appreciate that certain modifications can also be made to the present disclosure without departing from the scope of the same. For example, while clip 300 and luer 400 have been described herein as connecting to an end of tubing 124 that is connected to probe assembly 100, it is within the purview of the present disclosure to have clip 300 and luer 400 adapted to connect to an end of tube 124 that is connected to the coolant system 200. Here, clip 300 and luer 400 may operate and include structure similar to that as described hereinabove.

Clip 300 and/or luer 400 may be adapted to connect to one or more other clips 300 and/or luers 400. In this instance, one or more clips 300 and/or luers 400 may include interlocking interfaces configured to couple one or more clips together. This may be useful when tubing 124 is employed in limited working areas.

Clip housing 305 may have more than one channel 308. In this instance, one clip 300 may be employed to couple to multiple coolant lines (e.g., coolant lines that include in-flow and out-flow lines).

Although the present disclosure has been described with reference to a clip 300 including a clip housing 305 having a generally J-shape including first and second ends that converge toward each other, it is equally applicable to apply the concept of the present disclosure to a clip housing 305 having other shapes to support tubing 124. For example, clip housing 305 may have a C-shape, U-shape, M-shape, and so on (none of which is explicitly shown) each having respective ends converging toward each other and each having suitable radii at their respective converging locations.

While the structural and operative features of clip 300 and luer 400 have been described in terms of use with a single length of tubing, it is within the purview of the present disclosure to provide a clip 300 and luer 400 that may couple to coolant lines and/or cables that are housed within one cover, jacket, or sheath. Here, clip 300 and luer 400 may be configured similarly as described hereinabove, but may have components including respective openings that are configured to accommodate larger diameter structure.

Moreover, in the instance where coolant delivery systems employ luer type fittings that are configured to accommodate both the inflow and outflow tubing, clip housing 305 may have an additional, or larger diameter, opening 306 at the distal end of inner periphery 320, wherein two channels (not shown) may extend from opening 306, as described above with regard to channel 308, and accommodate both lengths of tubing. Here, a second opening (not shown), or other suitable structure, at second end 304 may be employed to maintain the lengths of tubing as described above.

Figure 6:
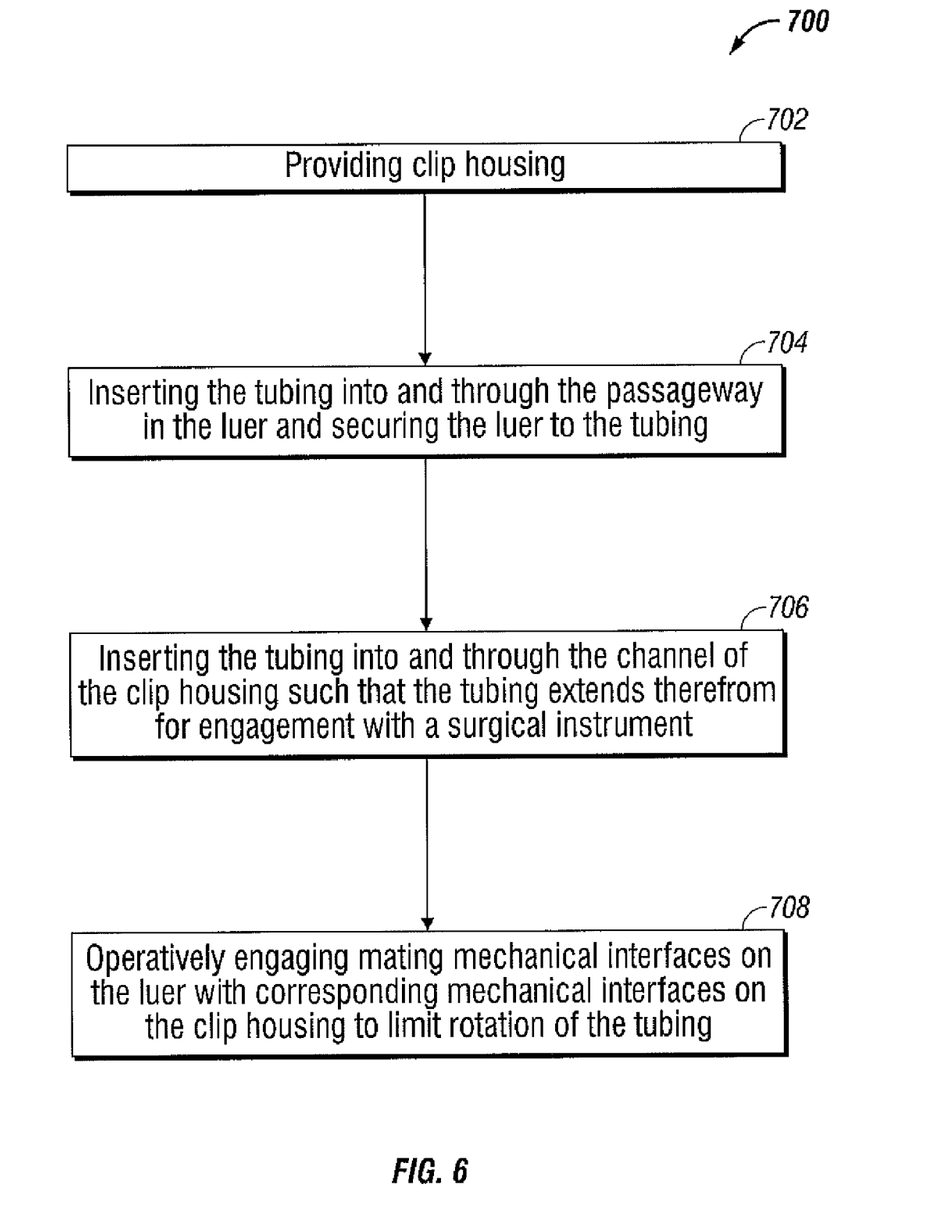
FIG. 6 is a flow chart of a method for preventing kinking in tubing in an electrosurgical cooling system in accordance with an embodiment of the present disclosure.

The present disclosure provides a method 700 of preventing kinking in tubing in a cooling system. At step 702, a clip housing having proximal and distal ends and a channel defined therethrough and a luer including a passageway defined therethrough is provided. The channel and the passageway are dimensioned to receive tubing for carrying a cooling fluid from a cooling source. At step 704, the tubing is inserted into and through the passageway in the luer and the luer is secured to the tubing. At step 706, the tubing is inserted into and through the channel of the clip housing such that the tubing extends therefrom for engagement with an instrument. And at step 708, mating mechanical interfaces on the luer are operatively engaged with corresponding mechanical interfaces on the clip housing to limit rotation of the tubing.

The present disclosure also provides a coolant delivery system for use with a microwave antenna. The coolant delivery system includes one or more lengths of tubing having one end adapted to connect to a microwave antenna and a second end adapted to connect to a coolant reservoir configured to store at least one type of coolant. The coolant delivery system includes a clip housing having proximal and distal ends and a channel defined therethrough. The channel configured to receive the one or more lengths tubing for carrying a cooling fluid from the coolant reservoir. The coolant delivery system also includes a luer that includes a passageway defined therethrough. The passageway is configured to securely receive the one or more lengths of tubing such that the tubing extends through the luer for reception within the channel defined in the clip housing. The luer includes one or more interfaces on a surface thereof that matingly engage a corresponding interface on the clip housing to limit rotation of the tubing.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A fluid clip for use with a coolant system, the fluid clip comprising:
   a clip housing having proximal and distal ends and a channel defined therethrough, the channel configured to receive tubing for carrying a cooling fluid from a cooling source;
   a luer including a passageway defined therethrough, the passageway configured to securely receive the tubing such that the tubing extends through the luer for reception within the channel defined in the clip housing, the luer including at least one interface on a surface thereof that matingly engages a corresponding interface on the clip housing to limit rotation of the tubing.

2. A fluid clip according to claim 1, wherein the interface on the luer includes a pair of opposing wings that matingly engage a corresponding pair of slots defined within the clip housing.

3. A fluid clip according to claim 1, wherein the luer includes a housing having a proximal flange that extends therefrom, the proximal flange moveable relative to the luer housing to secure the tubing within the passageway.

4. A fluid clip according to claim 3, wherein the luer housing including an inner peripheral surface that is configured to crimp the proximal flange upon reception therein, which, in turn, secures tubing within the passageway.

5. A fluid clip according to claim 1, wherein the luer includes a housing having a proximal flange that extends therefrom, the proximal flange including an inner peripheral surface that forms part of the passageway, the inner peripheral surface being dimensioned to securely engage the tubing when the tubing is received therethrough.

6. A fluid clip according to claim 1, wherein the clip housing is substantially J-shaped defining a radius at the distal end thereof.

7. A fluid clip according to claim 1, wherein the distal end of the clip housing includes a mechanical interface disposed thereon that facilitates secure engagement of the tubing therein.

8. A fluid clip according to claim 7, wherein the interface at the distal end of the clip housing includes a pair of opposing flanges that cooperate to facilitate secure engagement of the tubing to the distal end of the clip housing.

9. A fluid clip according to claim 7, wherein the interface at the distal end of the housing includes a pair of opposing flanges that cooperate in an overlapping manner to facilitate secure engagement of the tubing to the distal end of the clip housing.

10. A method of preventing kinking in tubing in a cooling system, comprising the steps of:
    providing a clip housing having proximal and distal ends and a channel defined therethrough and a luer including a passageway defined therethrough;
    inserting a tubing into and through the passageway in the luer and securing the luer to the tubing;
    inserting the tubing into and through the channel of the clip housing such that the tubing extends therefrom for engagement with an instrument;
    operatively engaging mechanical interfaces on the luer with corresponding mechanical interfaces on the clip housing to limit rotation of the tubing.

11. A method according to claim 10, wherein the step of inserting the tubing into and through the passageway in the luer includes the step of crimping a portion of the luer to secure the tubing.

12. A method according to claim 11, wherein the luer of the providing step includes a luer housing having a proximal flange that extends therefrom and the step of crimping includes the step of moving one of the luer housing and the proximal flange relative to one another to crimp the tubing.

13. A method according to claim 10, further comprising the step of operatively engaging the tubing in the distal end of the clip housing.

14. A method according to claim 10, further comprising the steps of:
    bending the tubing around a radius defined in the channel; and
    operatively engaging the tubing in the distal end of the clip housing to secure the tubing therein.

15. A coolant delivery system for use with a microwave antenna, comprising:
    at least one length of tubing having one end adapted to connect to a microwave antenna and a second end adapted to connect to a coolant reservoir configured to store at least one type of coolant;
    a clip housing having proximal and distal ends and a channel defined therethrough, the channel configured to receive the at least one length of tubing; and
    a luer including a passageway defined therethrough, the passageway configured to securely receive the at least one length of tubing such that the tubing extends through the luer for reception within the channel defined in the clip housing, the luer further including at least one interface on a surface thereof that matingly engages a corresponding interface on the clip housing to limit rotation of the tubing.

16. The coolant delivery system according to claim 15, wherein the interface on the luer includes a pair of opposing wings that matingly engage a corresponding pair of slots defined within the clip housing.

17. The coolant delivery system according to claim 15, wherein the luer includes a housing having a proximal flange that extends therefrom, the proximal flange moveable relative to the luer housing to secure the tubing within the passageway.

18. The coolant delivery system according to claim 17, wherein the luer housing including an inner peripheral surface that is configured to crimp the proximal flange upon reception therein, which, in turn, secures tubing within the passageway.

19. The coolant delivery system according to claim 15, wherein the luer includes a housing having a proximal flange that extends therefrom, the proximal flange including an inner peripheral surface that forms part of the passageway, the inner peripheral surface dimensioned to securely engage the tubing when the tubing is received therethrough.

20. The coolant delivery system according to claim 15, wherein the clip housing is substantially J-shaped defining a radius at the distal end thereof.

* * * * *